(12) United States Patent
Amthor et al.

(10) Patent No.: US 10,794,976 B2
(45) Date of Patent: Oct. 6, 2020

(54) MAGNETIC RESONANCE FINGERPRINTING DATA COLLECTION AND ANALYSIS SYSTEM

(71) Applicant: KONINKLIJKE PHILIPS N.V., Eindhoven (NL)

(72) Inventors: Thomas Erik Amthor, Eindhoven (NL); Sascha Krueger, Eindhoven (NL); Mariya Ivanova Donevea, Eindhoven (NL); Peter Koken, Eindhoven (NL); Julien Senegas, Eindhoven (NL); Jochen Keupp, Eindhoven (NL); Peter Boernert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 682 days.

(21) Appl. No.: 15/527,028

(22) PCT Filed: Nov. 16, 2015

(86) PCT No.: PCT/EP2015/076635
§ 371 (c)(1),
(2) Date: May 16, 2017

(87) PCT Pub. No.: WO2016/083166
PCT Pub. Date: Jun. 2, 2016

(65) Prior Publication Data
US 2017/0328973 A1 Nov. 16, 2017

(30) Foreign Application Priority Data
Nov. 27, 2014 (EP) .................................. 14195174

(51) Int. Cl.
*A61B 5/00* (2006.01)
*A61B 5/055* (2006.01)
(Continued)

(52) U.S. Cl.
CPC ..... *G01R 33/5608* (2013.01); *G01R 33/4828* (2013.01); *G16H 50/20* (2018.01);
(Continued)

(58) Field of Classification Search
CPC .......................... G01R 33/50; G01R 33/4828; G01R 33/5608; G01R 33/5602; A61B 5/055
See application file for complete search history.

(56) References Cited

U.S. PATENT DOCUMENTS 8,723,518 B2  5/2014 Seiberlich et al.
2008/0284433 A1  11/2008 Kraus et al.
(Continued)

FOREIGN PATENT DOCUMENTS

| WO | 2014047326 A1 | 3/2014 |
| WO | 2014062346 A1 | 4/2014 |
| WO | 2014099063 A1 | 6/2014 |

OTHER PUBLICATIONS

Ma, D. et al "Magnetic resonance fingerprinting." Nature. Mar. 14, 2013;495(7440):187-92. doi: 10.1038/nature11971.
(Continued)

*Primary Examiner* — Alesa Allgood

(57) ABSTRACT

A method of employing a central computer database (18) for supporting a characterization of tissue by magnetic resonance fingerprinting measurements, includes: exciting nuclei of a subject of interest by applying (50) a radio frequency excitation field $B_1$ generated according to a magnetic resonance fingerprinting sequence (38), acquiring (52) magnetic resonance imaging signal data from radiation emitted by excited nuclei of the subject of interest, transferring (54) a magnetic resonance fingerprinting data set (42) to the central computer database (18), retrieving (56) a predefined dictionary from the central computer database (18), matching (60) the acquired magnetic resonance imaging signal data to the retrieved dictionary by applying a
(Continued)

pattern recognition algorithm to determine a value (40) or a set of values (40) for at least one physical quantity ($T_1$, $T_2$), adding (62) at least the determined value (40) or the determined set of values (40) as a new entry of an associated medical data set (36) to the central computer database (18), and making (64) the new entry of an associated medical data set (36) accessible to users of the central computer database (18). A magnetic resonance fingerprinting data collection and analysis system (10) includes a central computer database, a data receiving unit (20), a data output unit (22) and a data analysis device (26) configured to carry out the method.

17 Claims, 4 Drawing Sheets

(51) Int. Cl.
| | | |
|---|---|---|
| *G01R 33/56* | (2006.01) | |
| *G16H 50/70* | (2018.01) | |
| *G16H 50/20* | (2018.01) | |
| *G01R 33/48* | (2006.01) | |
| *G06F 21/32* | (2013.01) | |
| *G01R 33/50* | (2006.01) | |
| *G06K 9/62* | (2006.01) | |

(52) U.S. Cl.
CPC ............ *G16H 50/70* (2018.01); *G01R 33/50* (2013.01); *G06F 21/32* (2013.01); *G06K 9/6232* (2013.01); *G06K 2209/05* (2013.01)

(56) References Cited

U.S. PATENT DOCUMENTS

| | | |
|---|---|---|
| 2012/0001631 A1 | 1/2012 | Espy et al. |
| 2012/0262165 A1 | 10/2012 | Griswold et al. |
| 2013/0265047 A1* | 10/2013 | Griswold ............... G01R 33/56 324/309 |
| 2014/0232399 A1 | 8/2014 | Griswold et al. |
| 2015/0023556 A1* | 1/2015 | Kim ..................... A61B 5/4064 382/103 |

OTHER PUBLICATIONS

Doneval et al "Compressed Sensing Reconstruction for Magnetic Resonance Parameter Mapping" Magnetic Resonance in Med. vol. 64, No. 4, Jun. 17, 2010 p. 1114-1120.

* cited by examiner

MAGNETIC RESONANCE FINGERPRINTING DATA COLLECTION AND ANALYSIS SYSTEM

CROSS REFERENCE TO RELATED APPLICATIONS

This application is a U.S. national phase application of International Application No. PCT/EP2015/076635, filed on Nov. 16, 2015, which claims the benefit of EP Application Serial No. 14195174.9 filed on Nov. 27, 2014 and is incorporated herein by reference.

FIELD OF THE INVENTION

The invention pertains to a method of employing a central computer database for supporting a characterization of tissue by magnetic resonance fingerprinting measurements, and a magnetic resonance fingerprinting data collection and analysis system comprising such central computer database.

BACKGROUND OF THE INVENTION

In the field of magnetic resonance imaging, a technique called magnetic resonance fingerprinting has recently been proposed in the article by Dan Ma et al., *Magnetic resonance fingerprinting*, Nature 495(7440), p. 187-192, 2013, doi: 10.1038/nature 11971. Therein, the concept of magnetic resonance fingerprinting (MRF) is described as making use of the fact that unique signal evolutions, or fingerprints, can be generated for different materials or tissues using an appropriate acquisition scheme called MRF sequence. This is possible through the continuous variation of the acquisition parameters throughout data collection. The temporal and spatial incoherence required in MRF can be achieved by varying acquisition parameters—such as the flip angle and phase of radio frequency pulses, the repetition time, echo time and sampling patterns—in a pseudorandom manner. Firstly, a dictionary is constructed, based on an MRF excitation sequence, containing signal evolutions from all foreseeable combinations of materials and system-related parameters. After the data are acquired, the separation of the signal into different material or tissue types can be achieved through applying a matching or pattern recognition algorithm to select a signal vector or a weighted set of signal vectors from the dictionary that best correspond to the observed signal evolution. All the parameters that were used to build this signal vector in the dictionary can then be retrieved simultaneously. In the article, it is noted that there are near-infinite possibilities for MRF-compatible excitation pulse sequences.

In U.S. patent application US 2013/0265047 A1, an apparatus, methods, and other embodiments associated with nuclear magnetic resonance (NMR) fingerprinting are described. One example NMR apparatus includes an NMR logic configured to repetitively and variably sample a (k, t, E) space associated with an object to acquire a set of NMR signals. Members of the set of NMR signals are associated with different points in the (k, t, E) space. Sampling is performed with t and/or E varying in a non-constant way. The varying parameters may include flip angle, echo time, RF amplitude, and other parameters. The NMR apparatus may also include a signal logic configured to produce an NMR signal evolution from the NMR signal, and a characterization logic configured to characterize a resonant species in the object as a result of comparing acquired signal to reference signal.

SUMMARY OF THE INVENTION

It is an object of the invention to provide a method of improved support for characterizing tissue by magnetic resonance fingerprinting measurements.

In one aspect of the present invention, the object is achieved by a method of employing a central computer database for supporting a characterization of tissue by magnetic resonance fingerprinting measurements.

The phrase "central computer database", as used in this application, shall be understood particularly as a computer database that is accessible from a plurality of external computer devices via a data communication link, such as, but not limited to, a local area network or via router communication link to the Internet.

The central computer database comprises a plurality of associated medical data sets. Each associated medical data set of the plurality of associated medical data sets includes at least an associated value or an associated set of values for at least one physical quantity.

The computer database further comprises a plurality of predefined dictionaries, wherein each predefined dictionary of the plurality of predefined dictionaries is dedicated to a specific magnetic resonance fingerprinting sequence and includes a plurality of possible magnetic resonance signal evolutions of nuclei having been excited according to the specific magnetic resonance fingerprinting sequence. Each magnetic resonance signal evolution of the plurality of possible magnetic resonance signal evolutions is based on a different value or a different set of values for the at least one physical quantity.

The method comprises steps of arranging at least a portion of a subject of interest in an examination space of a magnetic resonance imaging system in which a static magnetic field $B_0$ is being generated, exciting nuclei of or within at least the portion of the subject of interest by applying a radio frequency excitation field $B_1$ generated according to a magnetic resonance fingerprinting sequence, acquiring magnetic resonance imaging signal data from radiation emitted by the excited nuclei of or within at least the portion of the subject of interest, and transferring a magnetic resonance fingerprinting data set comprising at least the acquired magnetic resonance imaging signal data and the magnetic resonance fingerprinting sequence used to obtain the magnetic resonance imaging signal data to the central computer database.

Further, the method contains steps of retrieving a predefined dictionary of the plurality of predefined dictionaries which is based on the magnetic resonance fingerprinting sequence that has been used to obtain the magnetic resonance imaging signal data, if the dictionary that is based on the magnetic resonance fingerprinting sequence already exists in the central computer database, if a dictionary that is based on the magnetic resonance fingerprinting sequence is unavailable in the central computer database, creating a new dictionary, to be added to the plurality of predefined dictionaries as a new entry of a predefined dictionary to the central computer database, the new dictionary being dedicated to the magnetic resonance fingerprinting sequence that has been used to obtain the magnetic resonance imaging signal data and including a plurality of possible magnetic resonance signal evolutions of nuclei having been excited according to the magnetic resonance fingerprinting sequence, wherein each possible magnetic resonance signal evolution of the plurality of possible magnetic resonance signal evolutions is based on a different value or a different set of values for the at least one physical quantity, and retrieving the newly created dictionary, matching the acquired magnetic resonance imaging signal data to the retrieved dictionary by applying a pattern recognition algorithm to determine a value or a set of values for the at least one physical quantity from a possible magnetic resonance signal evolution of the plurality of possible magnetic resonance signal evolutions that forms the closest match with the acquired magnetic resonance imaging signal data with regard to a predefined mathematical measure function that is indicative of a difference between the magnetic resonance signal evolution based on the determined value or the determined set of values of the at least one physical quantity and the acquired magnetic resonance imaging signal data, adding at least the determined value or the determined set of values for the at least one physical quantity as a new entry of an associated medical data set to the plurality of associated medical data sets, wherein each physical quantity of the at least one physical quantity is either related to a physical property of a tissue type of at least the portion of the subject of interest or to a physical property of the magnetic resonance imaging system, and making the new entry of an associated medical data set accessible to users of the central-computer database.

In this way, a large number of associated medical data sets derived from measurements with various sources, i.e. magnetic resonance imaging systems, can be collected and stored in the central computer database, can be made accessible to potential users, and are available for further analysis, wherein the analysis can, in principle, involve the complete plurality of associated medical data sets. A possible source contributing to the central computer database may as well be a magnetic resonance imaging system that acquires magnetic resonance imaging signal data employing magnetic resonance fingerprinting sequences "on-the-fly", during other clinical examinations and without affecting workflow or image quality.

In one embodiment, the associated medical data sets of the plurality of associated medical data sets further includes the magnetic resonance fingerprinting sequence that has been used to obtain the magnetic resonance imaging signal data, and in the step of adding a new entry to the plurality of associated medical data sets, the new entry of an associated medical data set further comprises the magnetic resonance fingerprinting sequence that has been used to obtain the magnetic resonance imaging signal data. In this way, effects of different magnetic resonance fingerprinting sequences, for instance on an accuracy of determining the value or the set of values for the at least one physical quantity, can be analyzed from a subset of or from the complete plurality of associated medical data sets.

The step of making the new entry of associated medical data set accessible to users may encompass notifying the user of the magnetic resonance imaging system from which the magnetic resonance fingerprinting data set has been transferred to the central computer database, in this way establishing a way of feedback to the user. It may as well encompass providing the new entry of associated medical data set upon a specific request by the magnetic resonance imaging system from which the magnetic resonance fingerprinting data set has been transferred to the central computer database, or by a specific request of any of the users of magnetic resonance imaging systems that are configured to transfer magnetic resonance fingerprinting data sets.

In a preferred embodiment, the step of applying the radio frequency excitation field $B_1$ generated according to a magnetic resonance fingerprinting sequence includes a preceding step of providing the magnetic resonance fingerprinting sequence upon a specific request received from the magnetic resonance imaging system. In this way, the user of the magnetic resonance imaging system can benefit from experience derived from magnetic resonance fingerprinting measurements applied by other users of the central computer database. For instance, the specific request may be related towards a magnetic resonance fingerprinting sequence that has a high distinguishability, relative to other magnetic resonance fingerprinting sequences, with regard to one physical property or more physical properties that are of special interest to the user who forwarded the request.

In another preferred embodiment, the steps are carried out for each voxel out of a plurality of voxels that form at least a subset of a magnetic resonance image corresponding to the acquired magnetic resonance imaging signal data. In this way, an effective distinguishing between different types of tissue can be accomplished with a high spatial resolution.

Preferably, the at least one physical quantity is selected from a group that is formed by a longitudinal relaxation time of excited nuclei, a transverse relaxation time of excited nuclei, an off-resonance frequency of excited nuclei, a proton density of tissue, an electrical conductivity of tissue, a diffusion coefficient of tissue, a perfusion coefficient of tissue and a magnitude of a static magnetic field applied to nuclei. In this way, a multi-dimensional characterization can be accomplished which allows for distinguishing tissue in a large part of clinical applications.

In another preferred embodiment of the method, the step of adding an associated new entry of an associated medical data set to the plurality of associated medical data sets further comprises adding an assignment to at least one out of an organ, a tissue type or a tumor of a specific state to the associated new entry of an associated medical data set. For instance, a result of a histological report that may have been prepared well after acquiring the magnetic resonance fingerprinting signal data may be added as an assignment. The assignment may be manually added by a user of the magnetic resonance imaging system. In this way, the determined value or the determined set of values for the at least one physical quantity, the added assignment of tissue to a specific type of tissue and as the case may be, the magnetic resonance fingerprinting sequence, can be linked in the new entry of an associated medical data set and are available for further analysis. The tissue to which the added assignment has been made may be a voxel of the magnetic resonance image, or it may be a segmented region of the magnetic resonance image.

Preferably, the step of adding an assignment to the new entry of an associated medical data set to the plurality of associated medical data sets is subject to an affirmative authorization. This ensures that data are double-checked before the new entry of associated medical data set is added to the plurality of associated medical data sets, which enlarges reliability and credibility of the plurality of associated medical data sets. For instance, the affirmative authorization may be carried out by two clinicians in common at the magnetic resonance imaging system from which the magnetic resonance fingerprinting data set has been transferred to the central computer database. In another approach, a dedicated clinical review board may perform the affirmative authorization to ensure a diagnostic value being in line with the latest medical standards.

Similar benefits can be accomplished in another preferred embodiment, wherein the step of adding a newly created dictionary to the plurality of predefined dictionaries is subject to an affirmative authorization, which may be carried out as described above. Alternatively, any other step of affirmative authorization that appears to be suitable to the person skilled in the art may be applied.

In yet another preferred embodiment, the method comprises further steps of applying a machine learning algorithm to the plurality of associated medical data sets for determining correlations and/or relationships among the associated medical data sets, adding data indicative of the determined correlation and/or relationship to the associated medical data sets of the plurality of associated medical data sets, and making the added data accessible to users of the central computer database.

For instance, the machine learning algorithm may analyze associated medical data sets of the plurality of associated medical data sets comprising a substantially identical assignment to a tumor of a specific state and provide a statistical analysis on the associated value or the associated set of values for the at least one physical quantity. Any user of the central computer database may access the statistical analysis and may be provided with information about the statistical significance of the associated value or the associated set of values for the at least one physical quantity being related to a tumor of a specific state.

By way of example, the machine learning algorithm may analyze associated medical data sets of the plurality of associated medical data sets comprising a substantially identical assignment to a specific tissue type, and may provide a statistical analysis on an ability of the magnetic resonance fingerprinting sequences of the associated medical data sets to determine the at least one physical quantity; i.e. provide statistical information on a measurement error of the determined at least one physical quantity. The machine learning algorithm may then identify a magnetic resonance fingerprinting sequence as being especially appropriate for a precise determination of the at least one physical quantity of the specific tissue type, and may make the identified magnetic resonance fingerprinting sequence accessible to users of the central computer database.

In one embodiment, the method further comprises, within the step of applying the machine learning algorithm, a step of assigning weighting factors to associated medical data sets for which a correlation and/or a relationship is to be determined, if the correlation and/or the relationship was found between associated medical data sets derived from magnetic resonance fingerprinting data sets that have been transferred from different sources, to account for reliability and/or credibility of the transferred magnetic resonance fingerprinting data sets.

In this way, it can be ensured that the various types and capabilities of magnetic resonance imaging systems are accounted for in an analysis carried out by applying the machine learning algorithm.

In another aspect of the invention, a magnetic resonance fingerprinting data collection and analysis system is provided. The magnetic resonance fingerprinting data collection and analysis system comprises a central computer database, a data receiving unit, a data output unit and a data analysis system.

The central computer database is configured to store a plurality of associated medical data sets. Each associated medical data set of the plurality of associated medical data sets includes at least an associated value or an associated set of values for the at least one physical quantity. The central computer database is further configured to store a plurality of predefined dictionaries. Each predefined dictionary of the plurality of predefined dictionaries is dedicated to a specific magnetic resonance fingerprinting sequence and includes a plurality of possible magnetic resonance signal evolutions of nuclei that have been excited according to the specific magnetic resonance fingerprinting sequence. Each magnetic resonance signal evolution of the plurality of possible magnetic resonance signal evolutions is based on a different value or a different set of values for the at least one physical quantity.

The data receiving unit is configured to receive, from a plurality of magnetic resonance imaging systems, magnetic resonance fingerprinting data sets that comprise at least acquired magnetic resonance imaging signal data, acquired from excited nuclei of or within at least a portion of a subject of interest, and a magnetic resonance fingerprinting sequence used to obtain the magnetic resonance imaging signal data, and to transfer the received magnetic resonance fingerprinting data sets to the central computer database.

The data output unit that is configured for making data of the central computer database accessible for users of the magnetic resonance fingerprinting data collection and analysis system.

The data analysis device includes at least one processor unit and at least one digital memory unit. The data analysis device has data access to the plurality of associated medical data sets and to the plurality of predefined dictionaries. The data analysis device is configured to retrieve a predefined dictionary of the plurality of predefined dictionaries which is based on the magnetic resonance fingerprinting sequence that has been used to obtain the magnetic resonance imaging signal data, if the dictionary that is based on the magnetic resonance fingerprinting sequence already exists in the central computer database.

If a dictionary that is based on the magnetic resonance fingerprinting sequence is unavailable in the central computer database, the data analysis device is configured to create a new dictionary and to add the new dictionary to the plurality of predefined dictionaries as a new entry of a predefined dictionary to the central computer database. The new dictionary is dedicated to the magnetic resonance fingerprinting sequence that has been used to obtain the magnetic resonance imaging signal data and includes a plurality of possible magnetic resonance signal evolutions of nuclei having been excited according to the magnetic resonance fingerprinting sequence. Each possible magnetic resonance signal evolution of the plurality of possible magnetic resonance signal evolutions is based on a different value or a different set of values for the at least one physical quantity. In this case, the data analysis device is configured to retrieve the newly created dictionary.

Furthermore, the data analysis device is configured to match the acquired magnetic resonance imaging signal data to the retrieved dictionary by applying a pattern recognition algorithm to determine a value or a set of values for the at least one physical quantity from a possible magnetic resonance signal evolution of the plurality of possible magnetic resonance signal evolutions that forms the closest match with the acquired magnetic resonance imaging signal data with regard to a predefined mathematical measure function that is indicative of a difference between the magnetic resonance signal evolution based on the determined value or the determined set of values for the at least one physical quantity and the acquired magnetic resonance imaging signal data.

Then, the data analysis device is configured to add at least the determined value or the determined set of values for the at least one physical quantity as a new entry of an associated medical data set to the plurality of associated medical data sets in the central computer database. Each physical quantity of the at least one physical quantity is either related to a physical property of a tissue type of at least the portion of the subject of interest or to a physical property of a magnetic resonance imaging system of the plurality of magnetic resonance imaging systems.

At last, the data analysis device is configured to make the new entry of an associated medical data set accessible to the plurality of magnetic resonance imaging systems via the data output unit.

In a suitable embodiment of the magnetic resonance fingerprinting data collection and analysis system, the advantages described for the disclosed method apply and can be accomplished.

In one embodiment, the data analysis device is configured to further add the magnetic resonance fingerprinting sequence that has been used to obtain the magnetic resonance imaging signal data to the new entry of an associated medical data set of the plurality of associated medical data sets, such that the new entry of an associated medical data set comprises the magnetic resonance fingerprinting sequence that has been used to obtain the magnetic resonance imaging signal data and the determined value or the determined set of values for the at least one physical quantity. In this way, a subset of or the complete plurality of associated medical data sets can be available for analyzing effects of using different magnetic resonance fingerprinting sequences, for instance, on an accuracy of determining the value or the set of values for the at least one physical quantity.

In a preferred embodiment of the magnetic resonance fingerprinting data collection and analysis system, the central computer database is either server-based or cloud-based. In this way, a solution for receiving magnetic resonance fingerprinting data sets by the data receiving unit and for making data accessible for the plurality of magnetic resonance imaging systems can readily be provided.

In another preferred embodiment, the data receiving unit is configured to enable adding an assignment to at least one out of an organ, a tissue type or a tumor of a specific state to an associated medical data set of the plurality of associated medical data sets.

In this way, the determined value or the determined set of values for the at least one physical quantity, the added assignment of tissue to a specific type of tissue and, as the case may be, the magnetic resonance fingerprinting sequence, can be linked in the new entry of an associated medical data set and are available for further analysis.

Preferably, the enablement is subject to an affirmative authorization. This ensures that data are double-checked before the new entry of associated medical data set is added to the plurality of associated medical data sets, which enlarges reliability and credibility of the plurality of associated medical data sets.

In yet another preferred embodiment of the magnetic resonance fingerprinting data collection and analysis system, the data receiving unit is configured to receive requests from an external device on at least one out of a magnetic resonance fingerprinting sequence out of the plurality of associated medical data sets and a predefined dictionary of the plurality of predefined dictionaries, and wherein the data output unit is configured to make the requested data accessible to the external device upon the received requests.

With regard to further technical features and advantages of the magnetic resonance fingerprinting data collection and analysis system, reference is explicitly made herewith to the description related to the disclosed method, the figures and their corresponding figure captions, and vice versa.

In yet another aspect of the present invention, a software module is provided for carrying out steps of an embodiment of the disclosed method of employing the central computer database. The method steps to be conducted are converted into a program code of the software module, wherein the program code is implementable in a memory unit of the magnetic resonance fingerprinting data collection and analysis system and is executable by a processor unit of the magnetic resonance fingerprinting data collection and analysis system. The processor unit may be the processor unit of the data analysis device. The processor unit may, alternatively or supplementary, be another processor unit that is especially assigned to execute at least some of the method steps.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
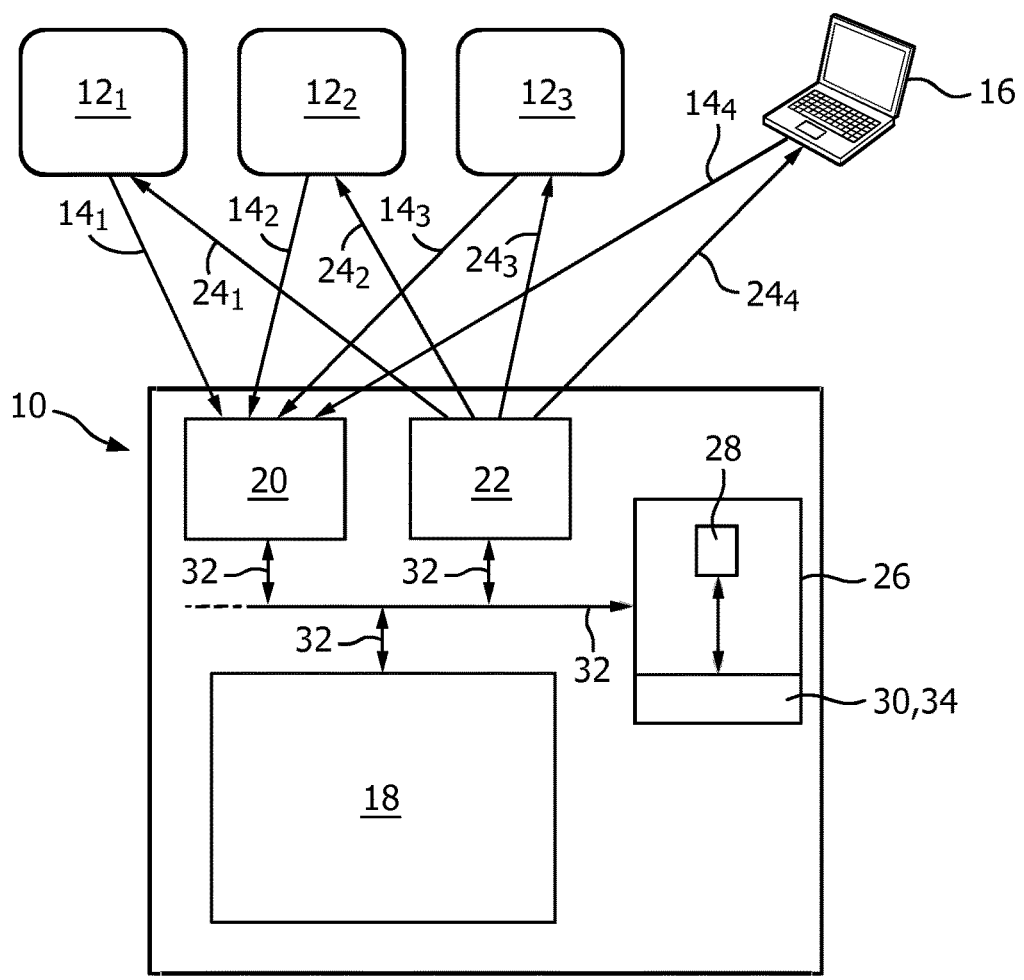
FIG. 1 shows a schematic configuration of an embodiment of a magnetic resonance fingerprinting data collection and analysis system in accordance with the invention, and interaction with potential users, FIG. 2 schematically illustrates results of determining a set of values for two distinct physical quantities from acquired magnetic resonance imaging signal data.

FIG. 1 shows a schematic configuration of an embodiment of a magnetic resonance fingerprinting data collection and analysis system 10 in accordance with the invention, and its interaction with potential users. The potential users are symbolized by a plurality of magnetic resonance imaging systems $12_1$, $12_2$, $12_3$. It is understood that the operators of the magnetic resonance imaging systems $12_1$, $12_2$, $12_3$ and/or clinicians who are employing the magnetic resonance imaging systems $12_1$, $12_2$, $12_3$ for the purpose of examination or who are involved in these are actually the potential users.

The data collection and analysis system 10 includes a central computer database 18, which is cloud-based, a data receiving unit 20, a data output unit 22 and a data analysis device 26, which in turn comprises a processor unit 28 and a digital memory unit 30.

Figure 2:
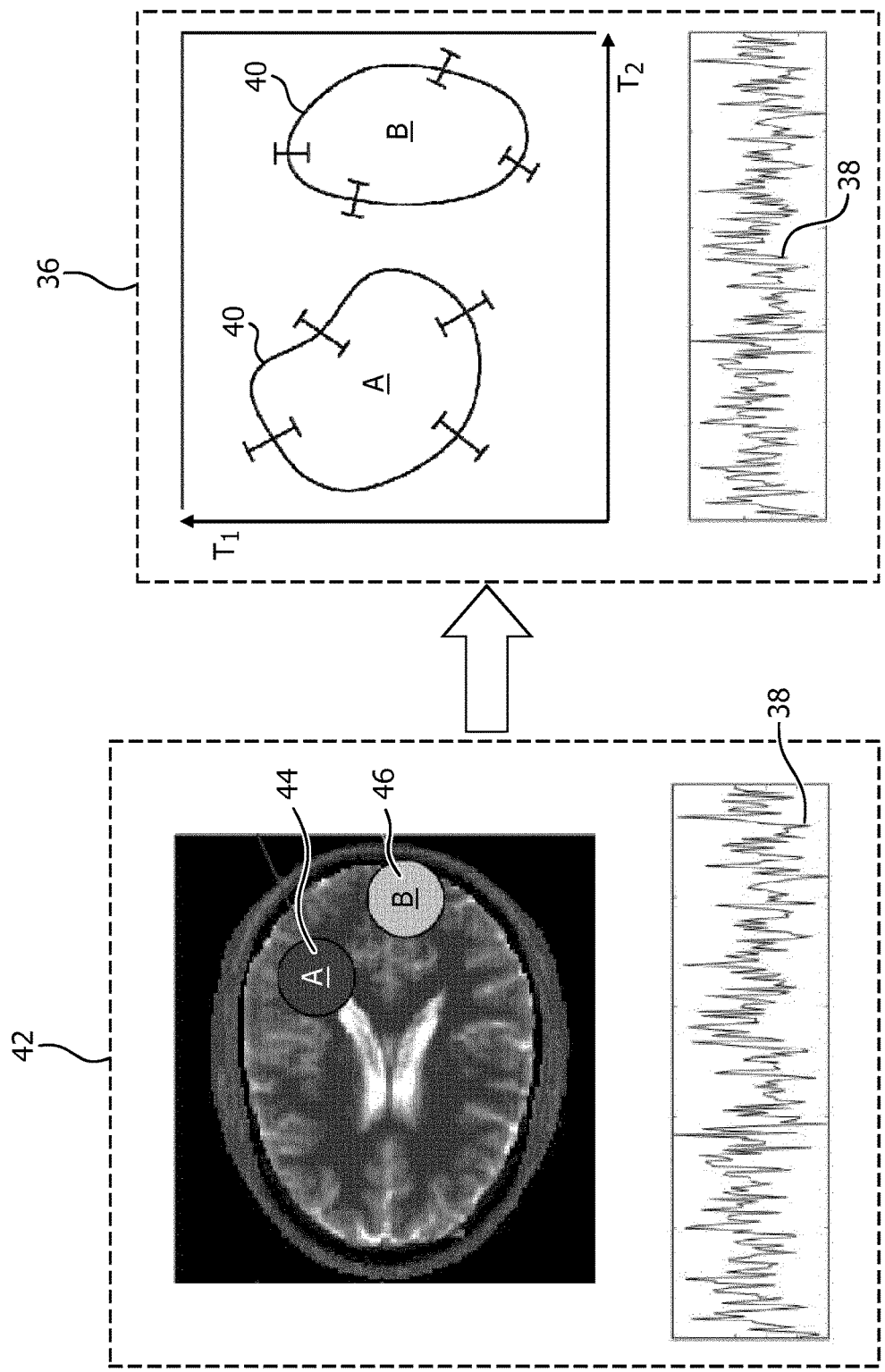

The central computer database 18 is configured to store a plurality of associated medical data sets. Each associated medical data set 36 of the plurality of associated medical data sets includes a magnetic resonance fingerprinting sequence 38 and an associated set of values 40 for at least two distinct physical quantities (FIG. 2).

The central computer database 18 is further configured to store a plurality of predefined dictionaries. Each predefined dictionary of the plurality of predefined dictionaries is dedicated to a specific magnetic resonance fingerprinting sequence 38 and includes a plurality of possible magnetic resonance signal evolutions of nuclei having been excited according to the specific magnetic resonance fingerprinting sequence 38, wherein each magnetic resonance signal evolution of the plurality of possible magnetic resonance signal evolutions is based on a different set of values 40 for the at least two distinct physical quantities.

Each physical quantity of the at least two distinct physical quantities is either related to a physical property of a tissue type of at least the portion of the subject of interest or to a physical property of a magnetic resonance imaging system $12_1$, $12_2$, $12_3$ of the plurality of magnetic resonance imaging systems $12_1$, $12_2$, $12_3$. By way of example, the at least two distinct physical quantities are given in this specific embodiment as the longitudinal relaxation time $T_1$ and the transverse relaxation time $T_2$ of a voxel of the magnetic resonance image that comprises the tissue type. In general, the at least two distinct physical quantities can be selected by a user from a group that is formed by the longitudinal relaxation time of excited nuclei, the transverse relaxation time of excited nuclei, an off-resonance frequency of excited nuclei, a proton density of tissue, an electrical conductivity of tissue, a diffusion coefficient of tissue, a perfusion coefficient of tissue and a magnitude of a static magnetic field applied to nuclei.

Each magnetic resonance imaging system $12_1$, $12_2$, $12_3$ of the plurality of magnetic resonance imaging systems $12_1$, $12_2$, $12_3$ comprises an examination space for arranging at least a portion of a subject of interest within, and a static magnetic field $B_0$ that is being generated at least in the examination space.

Each magnetic resonance imaging system $12_1$, $12_2$, $12_3$ of the plurality of magnetic resonance imaging systems $12_1$, $12_2$, $12_3$ is configured to excite nuclei of or within at least the portion of the subject of interest by applying a radio frequency excitation field $B_1$ generated according to a magnetic resonance fingerprinting sequence 38, and to acquire magnetic resonance imaging signal data from radiation emitted by the excited nuclei of or within at least the portion of the subject of interest.

Each magnetic resonance imaging system $12_1$, $12_2$, $12_3$ of the plurality of magnetic resonance imaging systems $12_1$, $12_2$, $12_3$ is further configured to transfer a magnetic resonance fingerprinting data set 42 comprising at least the acquired magnetic resonance imaging signal data and the magnetic resonance fingerprinting sequence 38 used to obtain the magnetic resonance imaging signal data to the central computer database 18.

To this end, each magnetic resonance imaging system $12_1$, $12_2$, $12_3$ of the plurality of magnetic resonance imaging systems $12_1$, $12_2$, $12_3$ is equipped with a data communication link $14_1$, $14_2$, $14_3$ which connects the magnetic resonance imaging system $12_1$, $12_2$, $12_3$ to the data receiving unit 20 for data communication. The data receiving unit 20 is configured to also receive further data communication links from computer devices 16 (one computer device 16 is exemplarily shown in FIG. 1) that are distinct from the magnetic resonance imaging systems $12_1$, $12_2$, $12_3$ and that are used by the operators of the magnetic resonance imaging systems $12_1$, $12_2$, $12_3$ and/or the clinicians. The data receiving unit 20 is configured to transfer the received magnetic resonance fingerprinting data sets 42 to the central computer database 18.

An example of a magnetic resonance fingerprinting data set 42 is illustrated in the left part of FIG. 2. In the magnetic resonance image corresponding to the acquired magnetic resonance imaging signal data, two spatial regions 44, 46 are marked, and the types of tissue disposed in the two spatial regions 44, 46 are labeled "tissue A" and "tissue B", respectively. Although the two spatial regions 44, 46 are shown as segmented regions of the magnetic resonance image, they may in general be as small as a single voxels. Shown below the magnetic resonance image is the magnetic resonance fingerprinting sequence 38 that had been used to obtain the magnetic resonance imaging signal data.

The data analysis device 26 has data access to the plurality of associated medical data sets 36 and to the plurality of predefined dictionaries via data communication links 32 that are arranged within the magnetic resonance fingerprinting data collection and analysis system 10.

The data output unit 22 is configured to provide data communication links $24_1$, $24_2$, $24_3$ between the central computer database 18 and users of the magnetic resonance fingerprinting data collection and analysis system 10 for making data of the central computer database 18 accessible to the users. Furthermore, FIG. 1 shows that a data communication link $24_4$ may as well be provided between the data output unit 22 and the computer device 16.

Figure 3:
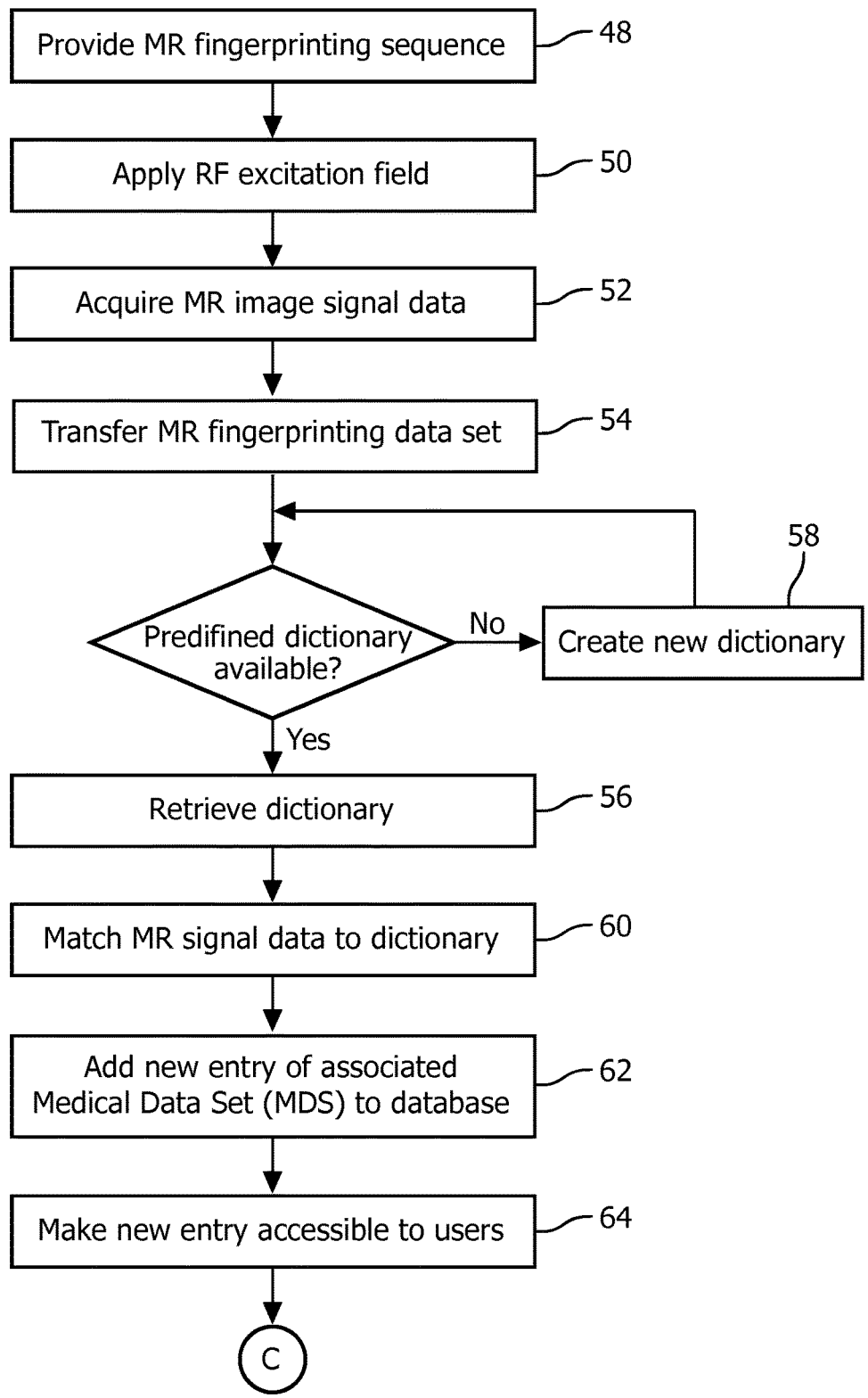
FIGS. 3 and 4 show a flow chart of an embodiment of the method in accordance with the invention.
Figure 4:
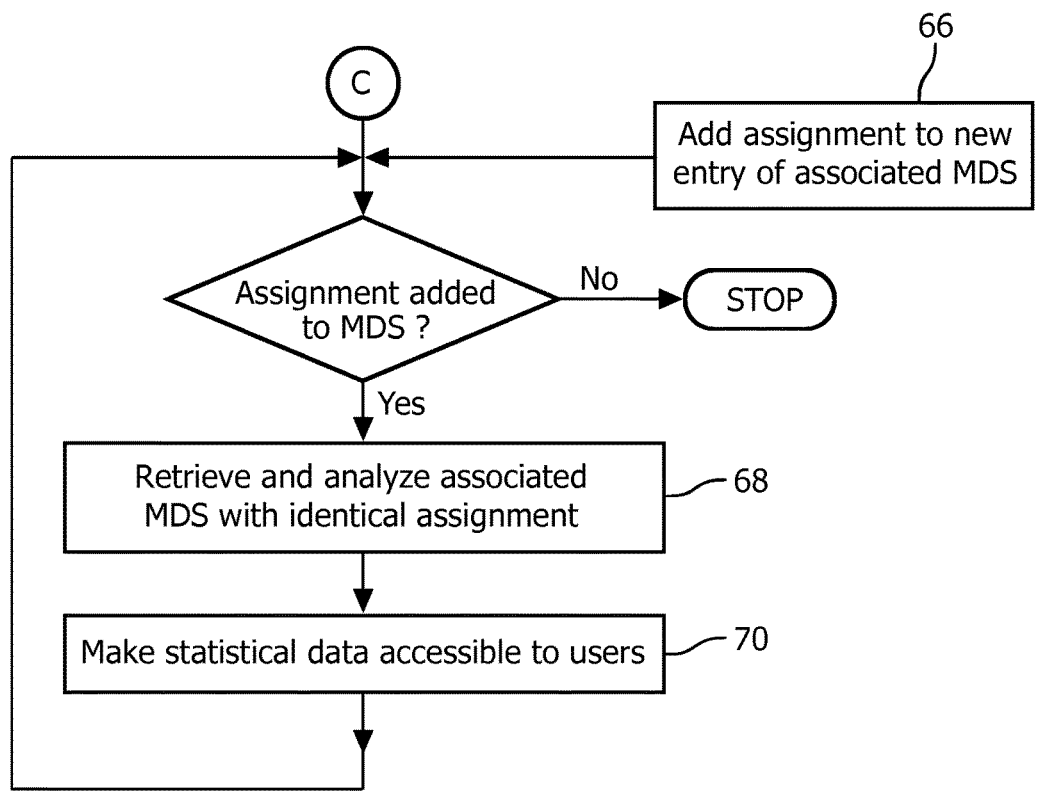

In the following, an embodiment of a method of employing the central computer database 18 for supporting a characterization of tissue by magnetic resonance fingerprinting measurements is described. A flow chart of the method is given in FIGS. 3 and 4. In preparation of employing the central computer database 18, it shall be understood that all involved units and devices are in an operational state and configured as illustrated in FIG. 1.

In order to be able to carry out parts of the method, the data analysis device 26 comprises a software module 34 (FIG. 1). The method steps to be conducted are converted into a program code of the software module 34, wherein the program code is implemented in the digital memory unit 30 of the data analysis device 26 and is executable by the processor unit 28 of the data analysis device 26. It shall further be understood that the magnetic resonance fingerprinting data collection and analysis system 10 is in a ready-to-operate state.

In a first step 48, the data analysis device 26 provides a magnetic resonance fingerprinting sequence 38 upon request by a magnetic resonance imaging system $12_1$, $12_2$, $12_3$ of the plurality of magnetic resonance imaging systems $12_1$, $12_2$, $12_3$.

In a next step 50, the provided magnetic resonance fingerprinting sequence 38 is used to generate and apply a radio frequency excitation field $B_1$ for exciting nuclei of or within the portion of the subject of interest.

In another step 52, magnetic resonance imaging signal data from radiation emitted by the excited nuclei of or within the portion of the subject of interest are acquired with the magnetic resonance imaging system $12_1$, $12_2$, $12_3$.

In a next step 54 then, a magnetic resonance fingerprinting data set 42 is transferred from the magnetic resonance imaging system $12_1$, $12_2$, $12_3$ to the central computer database 18. The magnetic resonance fingerprinting data set 42 comprises the acquired magnetic resonance imaging signal data and the magnetic resonance fingerprinting sequence 38 used to obtain the magnetic resonance imaging signal data.

In the following step 56, the data analysis device 26 retrieves a predefined dictionary of the plurality of predefined dictionaries which is based on the magnetic resonance fingerprinting sequence 38 that has been used to obtain the magnetic resonance imaging signal data, if the dictionary that is based on the magnetic resonance fingerprinting sequence 38 already exists in the central computer database 18.

If a dictionary that is based on the magnetic resonance fingerprinting sequence 38 is unavailable in the central computer database 18, the data analysis device 26 in another step 58 creates a new dictionary, which is to be added to the plurality of predefined dictionaries as a new entry of a predefined dictionary to the central computer database 18. The new dictionary is dedicated to the magnetic resonance fingerprinting sequence 38 that has been used to obtain the magnetic resonance imaging signal data and includes a plurality of possible magnetic resonance signal evolutions of nuclei having been excited according to the magnetic resonance fingerprinting sequence 38. Each possible magnetic resonance signal evolution of the plurality of possible magnetic resonance signal evolutions is based on a different set of values 40 for the two distinct physical quantities, given by the longitudinal relaxation time $T_1$ and the transverse relaxation time $T_2$. The newly created dictionary is then retrieved by the data analysis device 26.

In another step 60, the data analysis device 26 applies a pattern recognition algorithm for matching the acquired magnetic resonance imaging signal data to the retrieved dictionary. A set of values 40 for the two distinct physical quantities $T_1$ and $T_2$ is determined from the one of the possible magnetic resonance signal evolutions that forms the closest match with the acquired magnetic resonance imaging signal data with regard to a predefined mathematical measure function. The predefined mathematical measure function is indicative of a difference between the magnetic resonance signal evolution based on the determined set of values 40 for the distinct physical quantities and the acquired magnetic resonance imaging signal data. Appropriate mathematical measure functions are well known in the art and shall therefore not be discussed in more detail herein.

The step 60 of matching the acquired magnetic resonance imaging signal data to the retrieved dictionary is carried out for each voxel out of a plurality of voxels that form the subsets of the magnetic resonance image formed by the two spatial regions 44, 46 labeled "tissue A" and "tissue B", as shown in FIG. 2. In this way, the voxels of the subsets of the magnetic resonance image are mapped to a parameter space that is generated as a linear span of independent unit vectors, each independent unit vector representing one of the two distinct physical quantities. In FIG. 2, the independent unit vectors are arranged perpendicular to each other, and the generated parameter space is equivalent to a two-dimensional Cartesian coordinate space. If, in another possible embodiment, the set of values comprises more than two values for distinct physical quantities, the same concept is extended to as many dimensions as there are values for distinct physical quantities in the set of values 40.

As shown in FIG. 2, the mapping of the voxels of the subsets results in uncertainties that are also recorded and indicated by error bars.

In a following step 62, the data analysis device 26 adds the magnetic resonance fingerprinting sequence 38 and the determined set of values 40 for the two distinct physical quantities, including the determined uncertainties, as a new entry of an associated medical data set 36 to the plurality of associated medical data sets in the central computer database 18.

In another step 64 then, the data analysis device 26 makes the new entry of an associated medical data set 36 accessible to the users of the central computer database 18.

In another step 66 of the method, an assignment to a tumor of a specific state is added to the new entry of an associated medical data set 36. The data may be a result from a histological examination, data obtained with other clinical modalities or data that became available retrospectively after a successful therapy. The data is added to the new entry of an associated medical data set 36 by the user of the magnetic resonance imaging system $12_1$, $12_2$, $12_3$ that acquired the magnetic resonance fingerprinting signal data by accessing the associated medical data set 36 and manually adding the assignment.

The data analysis device 26 detects that the assignment has been added. As one of several options for initiation, this initiates a step 68 of retrieving and analyzing associated medical data sets 36 of the plurality of associated medical data sets which comprise an identical assignment to a tumor of a specific state. Other options (not shown in FIG. 4) for initiating this step 68 are putting forward a specific request by a user of the magnetic resonance fingerprinting data collection and analysis system 10, and a regular update procedure that is automatically run by the data analysis device 26.

As a result of the step 68 of analysis, the data analysis device 26 determines statistical data on the retrieved associated set of values 40 for the two distinct physical quantities, and statistical data indicating the ability of the magnetic resonance fingerprinting sequences 38 for determining the two distinct physical quantities.

Further, the data analysis device 26 makes the determined statistical data accessible to the users in another step 70. By forwarding requests to the magnetic resonance fingerprinting data collection and analysis system 10, users are able to obtain statistical data on the significance for a certain combination of values for distinct physical quantities derived from magnetic resonance fingerprinting signal data to be indicative of a tumor of a specific state. Upon request, users can be provided with magnetic resonance fingerprinting sequences 38 that are known to provide a high distinguishability for instance with regard to tumors in different specific states. In this way, the disclosed magnetic resonance fingerprinting data collection and analysis system 10 and the disclosed method of employing a central computer database 18 provide substantial support for characterization of tissue by magnetic resonance fingerprinting measurements.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST

| | |
|---|---|
| 10 | magnetic resonance fingerprinting data collection and analysis system |
| 12 | magnetic resonance imaging system |

-continued

REFERENCE SYMBOL LIST

| | |
|---|---|
| 14 | data communication link |
| 16 | computer device |
| 18 | central computer database |
| 20 | data receiving unit |
| 22 | data output unit |
| 24 | data communication link |
| 26 | data analysis device |
| 28 | processor unit |
| 30 | digital memory unit |
| 32 | data communication links |
| 34 | software module |
| 36 | associated medical data set |
| 38 | magnetic resonance fingerprinting sequence |
| 40 | set of values |
| 42 | magnetic resonance fingerprinting data set |
| 44 | region |
| 46 | region |

STEPS OF

| | |
|---|---|
| 48 | providing magnetic resonance fingerprinting sequence |
| 50 | applying RF excitation field |
| 52 | acquiring magnetic resonance imaging signal data |
| 54 | transferring magnetic resonance fingerprinting data set |
| 56 | retrieving predefined dictionary |
| 58 | creating new dictionary |
| 60 | matching magnetic resonance signal data to dictionary |
| 62 | adding new entry of associated medical data set |
| 64 | making new entry accessible for users |
| 66 | adding assignment to medical data set |
| 68 | retrieving and analyzing associated medical data sets |
| 70 | making statistical data accessible |
| $T_1$ | longitudinal relaxation time |
| $T_2$ | transverse relaxation time |

The invention claimed is:

1. A method of employing a central computer database for supporting a characterization of tissue by magnetic resonance fingerprinting measurements, the central computer database being configured to receive the magnetic resonance fingerprinting measurements from each of a plurality of distinct magnetic resonance imaging systems employed by a plurality of clinicians to perform magnetic resonance examination and to provide magnetic resonance fingerprinting data to the clinicians and other users, the central computer database comprising:

a plurality of associated medical data sets, each associated medical data set of the plurality of associated medical data sets including at least an associated value or an associated set of values for at least one physical quantity ($T_1$, $T_2$), and a plurality of predefined dictionaries, wherein each predefined dictionary of the plurality of predefined dictionaries is dedicated to a specific magnetic resonance fingerprinting sequence and includes a plurality of possible magnetic resonance signal evolutions of nuclei having been excited according to the specific magnetic resonance fingerprinting sequence, each magnetic resonance signal evolution of the plurality of possible magnetic resonance signal evolutions being based on a different value or a different set of values for the at least one physical quantity ($T_1$, $T_2$), the method comprising:

arranging at least a portion of a subject of interest in an examination space of a magnetic resonance imaging system in which a static magnetic field $B_0$ is being generated, exciting nuclei of or within at least the portion of the subject of interest by applying a radio frequency excitation field $B_1$ generated according to a magnetic resonance fingerprinting sequence, acquiring magnetic resonance imaging signal data from radiation emitted by excited nuclei of or within at least the portion of the subject of interest, transferring a magnetic resonance fingerprinting data set comprising at least the acquired magnetic resonance imaging signal data and the magnetic resonance fingerprinting sequence used to obtain the magnetic resonance imaging signal data, to the central computer database, searching for a predefined dictionary of the plurality of predefined dictionaries corresponding to the magnetic resonance fingerprinting sequence that has been used to obtain the magnetic resonance imaging signal data, if a dictionary that is based on the magnetic resonance fingerprinting sequence is unavailable in the central computer database:

creating a new dictionary and adding the new dictionary to the plurality of predefined dictionaries in the central computer database, the new dictionary being dedicated to the magnetic resonance fingerprinting sequence that has been used to obtain the corresponding magnetic resonance imaging signal data and including a plurality of possible magnetic resonance signal evolutions of nuclei having been excited according to the magnetic resonance fingerprinting sequence, wherein each possible magnetic resonance signal evolution of the plurality of possible magnetic resonance signal evolutions is based on a different value or a different set of values for the at least one physical quantity ($T_1$, $T_2$), if a corresponding dictionary that corresponds to the magnetic resonance fingerprinting sequence already exists in the central computer database:

matching the acquired magnetic resonance imaging signal data to the corresponding dictionary by applying a pattern recognition algorithm to determine a value or a set of values for the at least one physical quantity ($T_1$, $T_2$) from a possible magnetic resonance signal evolution of the plurality of possible magnetic resonance signal evolutions that forms the closest match with the acquired magnetic resonance imaging signal data with regard to a predefined mathematical measure function that is indicative of a difference between the magnetic resonance signal evolution based on the determined value or the determined set of values of the at least one physical quantity ($T_1$, $T_2$) and the acquired magnetic resonance imaging signal data, adding at least the determined value or the determined set of values for the at least one physical quantity ($T_1$, $T_2$) as a new entry of an associated medical data set to the plurality of associated medical data sets in the corresponding dictionary, wherein each physical quantity of the at least one physical quantity ($T_1$, $T_2$) is either related to a physical property of a tissue type of at least the portion of the subject of interest or to a physical property of the magnetic resonance imaging system, and making the added magnetic resonance fingerprinting data set accessible to users of the central computer database.

2. The method of claim 1, wherein each associated medical data set of the plurality of associated medical data sets further comprises the magnetic resonance fingerprinting sequence that has been used to obtain the magnetic resonance imaging signal data, and wherein in the step of adding a new entry of an associated medical data set to the plurality of associated medical data sets, the new entry of an associated medical data set further comprises the magnetic resonance fingerprinting sequence that has been used to obtain the magnetic resonance imaging signal data.

3. The method of claim 1, wherein the step of applying a radio frequency excitation field $B_1$ generated according to a magnetic resonance fingerprinting sequence includes a preceding step of providing the magnetic resonance fingerprinting sequence upon a specific request received from the magnetic resonance imaging system.

4. The method of claim 1, wherein the steps are carried out for each voxel out of a plurality of voxels that form at least a subset of a magnetic resonance image corresponding to the acquired magnetic resonance imaging signal data.

5. The method of claim 1, wherein the at least one physical quantity ($T_1$, $T_2$) is selected from a group that is formed by a longitudinal relaxation time of excited nuclei ($T_1$), a transverse relaxation time ($T_2$) of excited nuclei, an off-resonance frequency of excited nuclei, a proton density of tissue, an electrical conductivity of tissue, a diffusion coefficient of tissue, a perfusion coefficient of tissue and a magnitude of a static magnetic field applied to nuclei.

6. The method of claim 1, wherein the step of adding a newly created dictionary to the plurality of predefined dictionaries is subject to an affirmative authorization.

7. A software module for carrying out the method of claim 1, wherein the method steps to be conducted are converted into a program code of the software module, wherein the program code is implementable in a digital memory unit of the magnetic resonance fingerprinting data collection and analysis system and is executable by a processor unit of magnetic resonance fingerprinting data collection and analysis system.

8. A non-transitory computer-readable medium carrying software configured to control a processor unit to perform the method of claim 1.

9. The method of claim 1, wherein the step of adding a new entry of an associated medical data set to the plurality of associated medical data sets further comprises adding an assignment to at least one out of an organ, a tissue type or a tumor of a specific state to the associated new entry of an associated medical data set.

10. The method of claim 9, wherein the step of adding an assignment to the new entry of an associated medical data set to the plurality of associated medical data sets is subject to an affirmative authorization.

11. The method of claim 1, further comprising:
applying a machine learning algorithm to the plurality of associated medical data sets for determining correlations and/or relationships among the associated medical data sets,
adding data indicative of the determined correlation and/or relationship to the associated medical data sets of the plurality of associated medical data sets, and
making the added data accessible to users of the central computer database.

12. The method as claimed in claim 11, further comprising, within the step of applying the machine learning algorithm, a step of assigning weighting factors to associated medical data sets for which a correlation and/or a relationship is to be determined, if the correlation and/or the relationship was found between associated medical data sets derived from magnetic resonance fingerprinting data sets that have been transferred from different sources, to account for reliability and/or credibility of the transferred magnetic resonance fingerprinting data sets.

13. A magnetic resonance fingerprinting data collection and analysis system, comprising:
a central computer database that is configured to store:
a plurality of associated medical data sets, each associated medical data set of the plurality of associated medical data sets including at least an associated value or an associated set of values for the at least one physical quantity ($T_1$, $T_2$), and
a plurality of predefined dictionaries, wherein each predefined dictionary of the plurality of predefined dictionaries is dedicated to a specific magnetic resonance fingerprinting sequence and includes a plurality of possible magnetic resonance signal evolutions of nuclei having been excited according to the specific magnetic resonance fingerprinting sequence, each magnetic resonance signal evolution of the plurality of possible magnetic resonance signal evolutions being based on a different value or a different set of values for the at least one physical quantity ($T_1$, $T_2$),
a data receiving unit configured to receive, from a plurality of distinct magnetic resonance imaging systems, magnetic resonance fingerprinting data sets comprising at least acquired magnetic resonance imaging signal data, acquired from excited nuclei of or within at least a portion of a subject of interest, and a magnetic resonance fingerprinting sequence used to obtain the magnetic resonance imaging signal data, and to transfer the received magnetic resonance fingerprinting data sets to the central computer database,
a data output unit that is configured for making data of the central computer database accessible for users,
a data analysis device including at least one processor unit and at least one digital memory unit, the data analysis device having data access to the plurality of associated medical data sets and to the plurality of predefined dictionaries, wherein the data analysis device is configured to:
in response to the data receiving unit receiving a magnetic resonance fingerprinting data set, determining whether a predefined dictionary of the plurality of predefined dictionaries corresponding to the magnetic resonance fingerprinting sequence of the received magnetic resonance fingerprinting data set already exists in the central computer database,
if a dictionary corresponding to the received magnetic resonance fingerprinting sequence does not exist in the central computer database:
create a new dictionary and to add the new dictionary to the plurality of predefined dictionaries to the central computer database, the new dictionary being dedicated to the magnetic resonance fingerprinting sequence that has been used to obtain the magnetic resonance imaging signal data and including a plurality of possible magnetic resonance signal evolutions of nuclei having been excited according to the magnetic resonance fingerprinting sequence, wherein each possible magnetic resonance signal evolution of the plurality of possible magnetic resonance signal evolutions is based on a different value or a different set of values for the at least one physical quantity (T1, T2),
if a dictionary corresponding to the received magnetic resonance fingerprinting sequence does exist in the central computer database:
match the acquired magnetic resonance imaging signal data to the corresponding dictionary by applying a pattern recognition algorithm to determine a value or a set of values for the at least one physical quantity ($T_1$, $T_2$) from a possible magnetic resonance signal evolution of the plurality of possible magnetic resonance signal evolutions that forms the closest match with the acquired magnetic resonance imaging signal data with regard to a predefined mathematical measure function that is indicative of a difference between the magnetic resonance signal evolution based on the determined value or the determined set of values of the at least one physical quantity ($T_1$, $T_2$) and the received magnetic resonance imaging signal data,
add at least the determined value or the determined set of values for the at least one physical quantity ($T_1$, $T_2$) as a new entry of an associated medical data set to the plurality of associated medical data sets in the corresponding dictionary of the central computer database,
wherein each physical quantity of the at least one physical quantity ($T_1$, $T_2$) is either related to a physical property of a tissue type of at least the portion of the subject of interest or to a physical property of a magnetic resonance imaging system of the plurality of magnetic resonance imaging systems, and
make the new entry of an associated medical data set accessible to the plurality of magnetic resonance imaging systems via the data output unit.

14. The magnetic resonance fingerprinting data collection and analysis system of claim 13, wherein the central computer database is either server-based or cloud-based.

15. The magnetic resonance fingerprinting data collection and analysis system of claim 13, wherein the data receiving unit is configured to receive requests from an external device on at least one out of a magnetic resonance fingerprinting sequence of an associated medical data set out of the plurality of associated medical data sets and a predefined dictionary of the plurality of predefined dictionaries, and wherein the data output unit is configured to make the requested data accessible to the external device upon the received requests.

16. The magnetic resonance fingerprinting data collection and analysis system of claim 13, wherein the data receiving unit is configured to enable adding an assignment to at least one out of an organ, a tissue type or a tumor of a specific state to an associated medical data set of the plurality of associated medical data sets.

17. The magnetic resonance fingerprinting data collection and analysis system of claim 16, wherein the enablement is subject to an affirmative authorization.

* * * * *